United States Patent
Soni

(10) Patent No.: US 10,111,700 B2
(45) Date of Patent: Oct. 30, 2018

(54) SURGICAL INSTRUMENTS INCLUDING 3D INJECTION MOLDED ELECTRICAL CIRCUITS AND CONNECTIONS

(71) Applicant: COVIDIEN LP, Mansfield, MA (US)

(72) Inventor: Purvish Soni, Abington, MA (US)

(73) Assignee: COVIDIEN LP, Mansfield, MA (US)

( * ) Notice: Subject to any disclaimer, the term of this patent is extended or adjusted under 35 U.S.C. 154(b) by 920 days.

(21) Appl. No.: 14/516,254

(22) Filed: Oct. 16, 2014

(65) Prior Publication Data
US 2015/0133928 A1     May 14, 2015

Related U.S. Application Data

(60) Provisional application No. 61/902,013, filed on Nov. 8, 2013.

(51) Int. Cl.
*A61B 18/18* (2006.01)
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00083* (2013.01); *A61B 2018/00595* (2013.01); *A61B 2018/00607* (2013.01); *A61B 2018/1455* (2013.01); *Y10T 29/49117* (2015.01)

(58) Field of Classification Search
CPC ........ A61B 18/1445; A61B 2018/1455; A61B 2018/00083; A61B 2018/0063; A61B 2018/00607; A61B 2018/00595; Y10T 29/49117
See application file for complete search history.

(56) References Cited

U.S. PATENT DOCUMENTS

| | | | |
|---|---|---|---|
| 9,649,151 B2* | 5/2017 | Goodman | A61B 18/1445 |
| 2004/0116924 A1* | 6/2004 | Dycus | A61B 18/1445 606/51 |
| 2010/0179540 A1* | 7/2010 | Marczyk | A61B 18/1445 606/41 |
| 2011/0303644 A1 | 12/2011 | Macary | |

OTHER PUBLICATIONS www.selectconnecttech.com, SelectConnect Technologies, 3D Circiuts by Laser Direct Structuring, last visited Dec. 30, 2014.

* cited by examiner

*Primary Examiner* — Rex R Holmes

(57) ABSTRACT

An end effector assembly includes a first jaw member and a second jaw member. The first and second jaw members are operably movable relative to one another between an open position and a clamped position. The first and second jaw members each include an electrically conductive plate. The electrically conductive plates of the first and second jaw members oppose each other and are configured to conduct energy through tissue clamped therebetween. The first jaw member further includes an insulative spacer having a rib and a conductive strip. The rip extends from a surface of the insulative spacer towards the electrically conductive plate. The conductive strip is integrally formed on a surface of the rib to contact the electrically conductive plate. The conductive strip is configured to transmit an electrical potential to the electrically conductive plate.

10 Claims, 8 Drawing Sheets

SURGICAL INSTRUMENTS INCLUDING 3D INJECTION MOLDED ELECTRICAL CIRCUITS AND CONNECTIONS

CROSS REFERENCE TO RELATED APPLICATION

The present application claims the benefit of and priority to U.S. Provisional Application Ser. No. 61/902,013, filed on Nov. 8, 2013, the entire contents of which are incorporated herein by reference.

BACKGROUND

1. Technical Field

The present disclosure relates to surgical instruments and, more specifically, to surgical instruments including multi-shot 3D injection molded electrical circuits and connections.

2. Discussion of Related Art

Electrosurgical forceps utilize both mechanical clamping action and electrical energy to affect hemostasis by heating tissue to coagulate, cauterize, and/or seal tissue. As an alternative to open forceps for use with open surgical procedures, many modern surgeons use endoscopes and endoscopic instruments for remotely accessing tissue through smaller, puncture-like incisions. As a direct result thereof, patients tend to benefit from less scarring and reduced healing time.

Due to the inherent spatial considerations of endoscopic surgical procedures, instrument manufacturers are presented with a design challenge, that is, to find ways to make electrosurgical instruments that fit through smaller cannulas or openings in tissue. Manufacturers strive to overcome these challenges by developing ways to incorporate electrical circuits, circuit components, and connections together with the necessary mechanical components into a small, compact instrument.

In particular, manufacturers have been able to provide smaller circuit boards with more compact circuit layouts by significantly manipulating and reducing the size of individual components. However, as devices become smaller and more compact, it is increasingly difficult to manufacture such circuitry and to simultaneously keep the cost of manufacturing relatively low. It is also an ongoing challenge to build smaller electronics without detrimentally effecting reliability and performance of the product.

SUMMARY

In an aspect of the present disclosure, an end effector assembly includes a first jaw member and a second jaw member. The first and second jaw members are operably moveable relative to one another between an open position and a clamped position. The first jaw member includes a first electrically conductive plate and the second jaw member includes a second electrically conductive plate. The first and second electrically conductive plates oppose each other. The first and second electrically conductive plates are configured to conduct energy through tissue clamped therebetween. The first jaw member includes a first insulative spacer having a rib and a conductive strip. The rib extends from a surface of the first insulative spacer towards the first electrically conductive plate. The conductive strip is internally formed on a surface of the rib contacting the first electrically conductive plate. The conductive strip is configured to transmit a first electrical potential to the first electrically conductive plate. In aspects, the second jaw member is fixed and the first jaw member is moveable.

In aspects of the present disclosure, the second jaw member includes a second insulative spacer having a rib and a conductive strip. The rib extending from a surface of the second insulative spacer towards the second electrically conductive plate. The conductive strip is integrally formed on a surface of the rib contacting the second electrically conductive plate. The conductive strip is configured to transmit a second electrical potential to the second electrically conductive plate.

In aspects of the present disclosure, the housing includes a first electrical path and a second electrical path. The first and second electrical paths are integrally formed on an inner surface of the housing. The first electrical path is configured to transmit the first electrical potential to the conductive strip of the first insulative spacer and the second electrical path is configured to transmit the second electrical potential to the conductive strip of the second insulative spacer. In aspects, the surgical instrument includes a rotating assembly having a tube disposed within the housing and the shaft. The tube includes first and second tube contacts disposed on a proximal end of thereof. The first tube contact is selectively electrically couplable with the first electrical path for transmitting the first electrical potential from the first electrical path to the conductive strip of the first insulative spacer. The second tube contact is selectively electrically couplable with the second electrical path for transmitting the second electrical potential from the second electrical path to the conductive strip of the second insulative spacer. In some aspects, the surgical instrument includes first and second electrical leads. The first electrical lead is electrically coupled to the first tube contact and electrically coupled to the conductive strip of the first insulative spacer for transmitting the first electrical potential from the first electrical path to the first electrically conductive plate. The second electrical lead is electrically coupled to the second tube contact and electrically coupled to the conductive strip of the second insulative spacer for transmitting the second electrical potential from the second electrical path to the second electrically conductive plate. In aspects, the first and second electrical leads are disposed within the tube of the rotating assembly. In certain aspects, the surgical instrument includes an electrosurgical cable for transmitting energy from a generator to the instrument. The first and second electrical paths being disposed between the electrosurgical cable and the first and second tube contacts respectively.

In aspect of the present disclosure, a surgical instrument is provided including a housing, a shaft, and the end effector assembly according to any of the above aspects. The shaft extends distally from the housing. The end effector assembly is positioned at the distal end of the shaft.

In aspects of the present disclosure, a method of manufacturing an end effector assembly including forming an insulative spacer of a non-conductive material, creating a rib on a surface of the insulative spacer, and metalizing the rib with a conductive material to integrally form a conductive strip on a surface of the rib. Metalizing may include dipping the rib in an electroless bath to form the conductive strip. Creating the rip may include palladium and metalizing may include bonding the conductive material to the palladium.

In aspects of the present disclosure, the method includes engaging the conductive strip with an electrically conductive plate. The method may include engaging the electrically conducive plate with a cover to form a jaw member. The insulative spacer may be positioned between the cover and the electrically conductive plate such that the cover maintains the conductive strip in engagement with the electrically conductive plate.

In aspects of the present disclosure, the method includes forming a first jaw member and a second jaw member moveable relative to one another and the electrical conductive plate of the first jaw member opposes the electrically conductive plate of the second jaw member.

In aspects of the present disclosure, a first shot of a non-conductive material is injected into a mold to form the insulative spacer. A second shot including palladium may be injected into a mold to form the rib on a surface of the insulative spacer.

By integrally forming electrical paths on the surface of a non-conductive material, plastic components may be miniaturized. This miniaturization may enable electronic devices to be lighter, smaller, and more portable. This miniaturization may also allow parts to be made faster, easier, more reliably, and more cost effectively. Another advantage may be reducing the component count of surgical instruments enabling simplified assembly.

Certain aspects of the present disclosure may include some, all, or none of the above advantages. One or more other technical advantages may be readily apparent to those skilled in the art for the figures, descriptions, and claims included herein.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
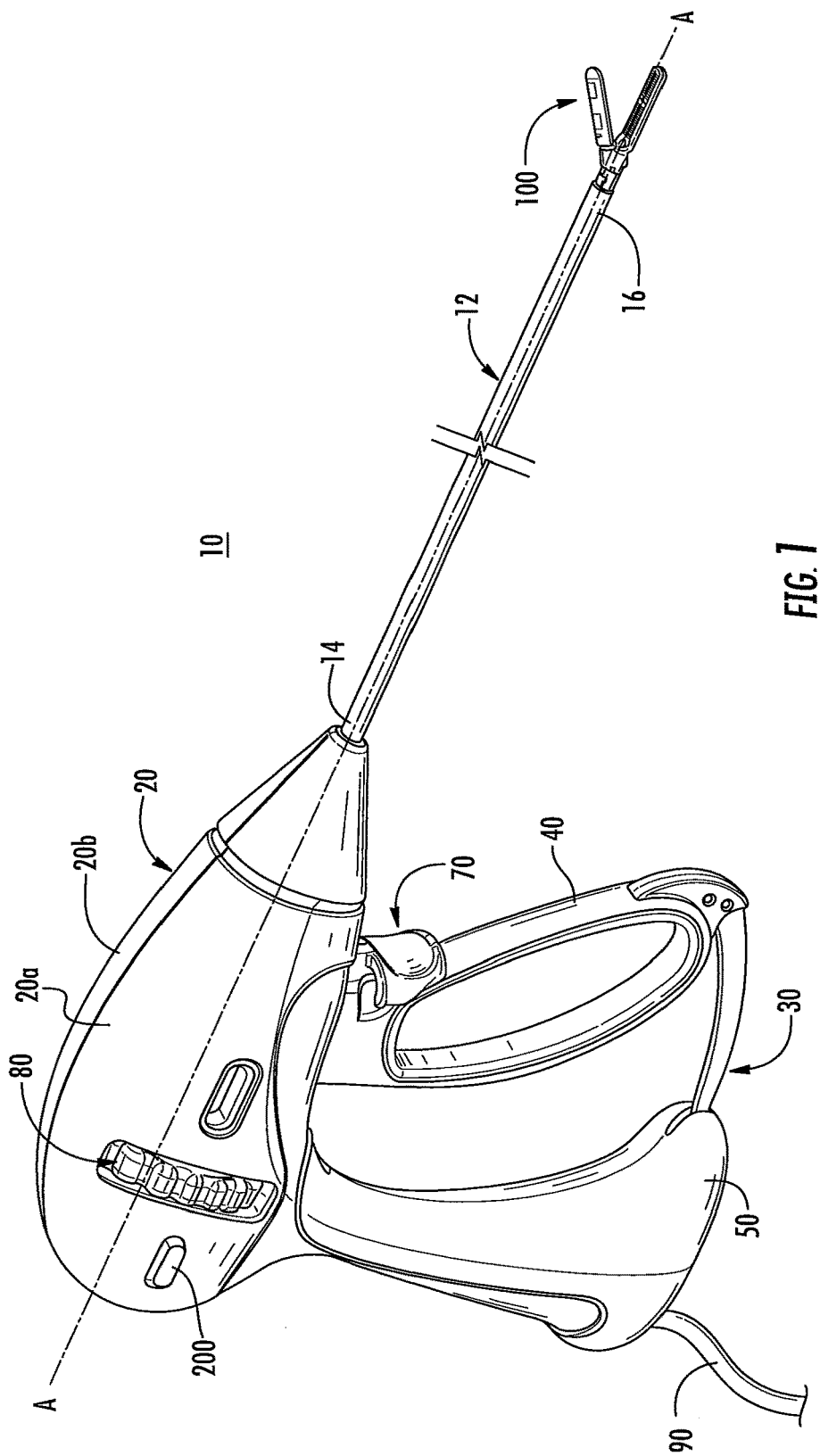
FIG. 1 is a perspective view of an exemplary embodiment of a surgical instrument provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is furthest from the clinician.

With reference to FIG. 1, an exemplary embodiment of a surgical instrument 10 is provided in accordance with the present disclosure including a housing 20, a handle assembly 30, a rotating assembly 80, a trigger assembly 70, and an end effector assembly 100 that mutually cooperate to grasp, treat, e.g., seal, and divide tissue.

The surgical instrument 10 further includes a shaft 12 that has a distal end 16 dimensioned to mechanically engage the end effector assembly 100 and a proximal end 14 that mechanically engages the housing 20.

Continuing to refer to FIG. 1, the surgical instrument 10 also includes an electrosurgical cable 90 that connects the instrument 10 to a generator (not shown). Cable 90 transmits electrosurgical energy through the surgical instrument 10 to the end effector assembly 100.

The handle assembly 30 includes a fixed handle 50 and a movable handle 40. Fixed handle 50 is integrally associated with housing 20 and handle 40 is movable relative to fixed handle 50. Rotating assembly 80 is integrally associated with the housing 20 and is continuously rotatable in either direction about a longitudinal axis "A-A." The housing 20 includes two halves 20a and 20b that house the internal working components of the surgical instrument 10.

Figure 2:
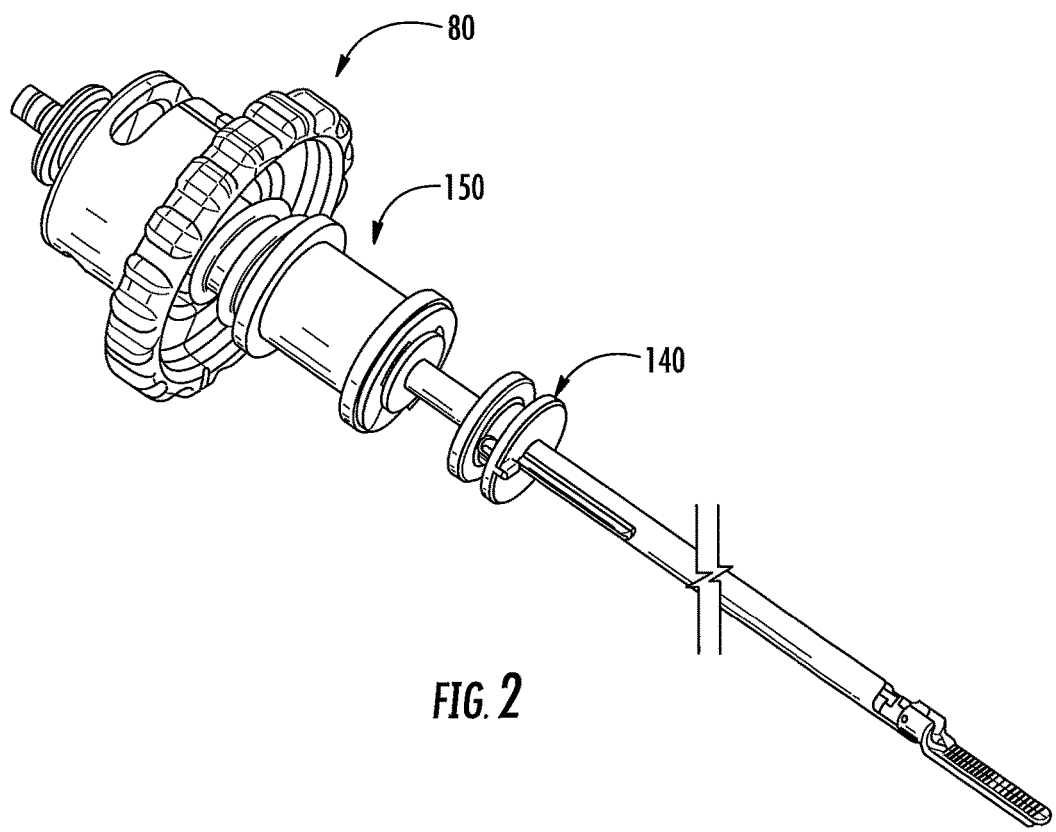
FIG. 2 is a perspective view of the inner assembly of the surgical instrument shown in FIG. 1 operably coupled to a shaft and a jaw member of the surgical instrument.

Referring also to FIG. 2, an inner assembly operably disposed within housing 20 of instrument 10 includes a rotating assembly 80, a drive assembly 150, and a knife assembly 140. Movable handle 40 and trigger assembly 70 are operatively connected to the housing 20 and the fixed handle 50 and are operable to selectively actuate drive assembly 150 and knife assembly 140, respectively.

Figure 3:
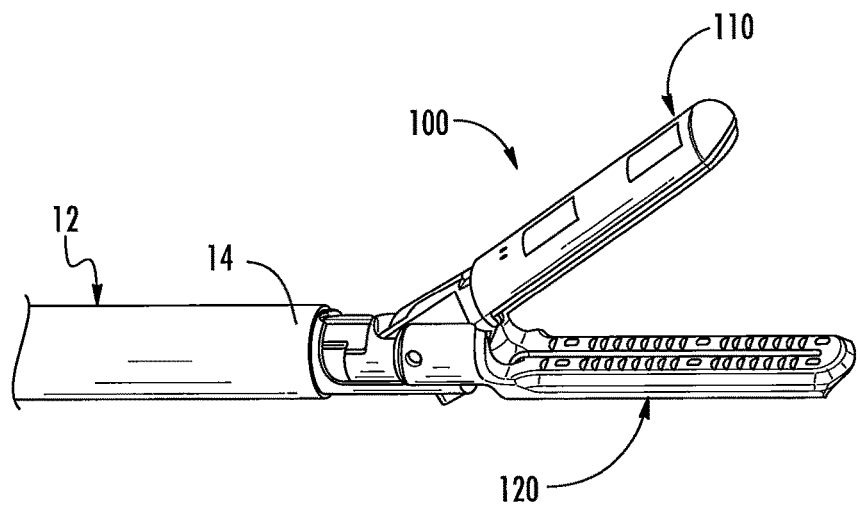
FIG. 3 is a side perspective view of an end effector assembly of the surgical instrument shown in FIG. 1.

With reference to FIG. 3, end effector assembly 100 is attached at the distal end 14 of shaft 12 and includes a pair of opposing jaw members 110 and 120. Movable handle 40 of handle assembly 30 is ultimately connected to drive assembly 150 (FIG. 2) to impart movement of the jaw members 110 and 120 relative to one another between an open position and a clamped or closed position. More specifically, movable handle 40 (FIG. 1) is selectively moveable between a first position relative to fixed handle 50 (FIG. 1) and a second position in closer proximity to the fixed handle 50. The jaw members 110, 120 are in the open position (FIG. 3) when the moveable handle 40 is in the first position and the jaw members 110, 120 are in the closed position (not shown) when the moveable handle 40 is in the second position.

Figure 4:
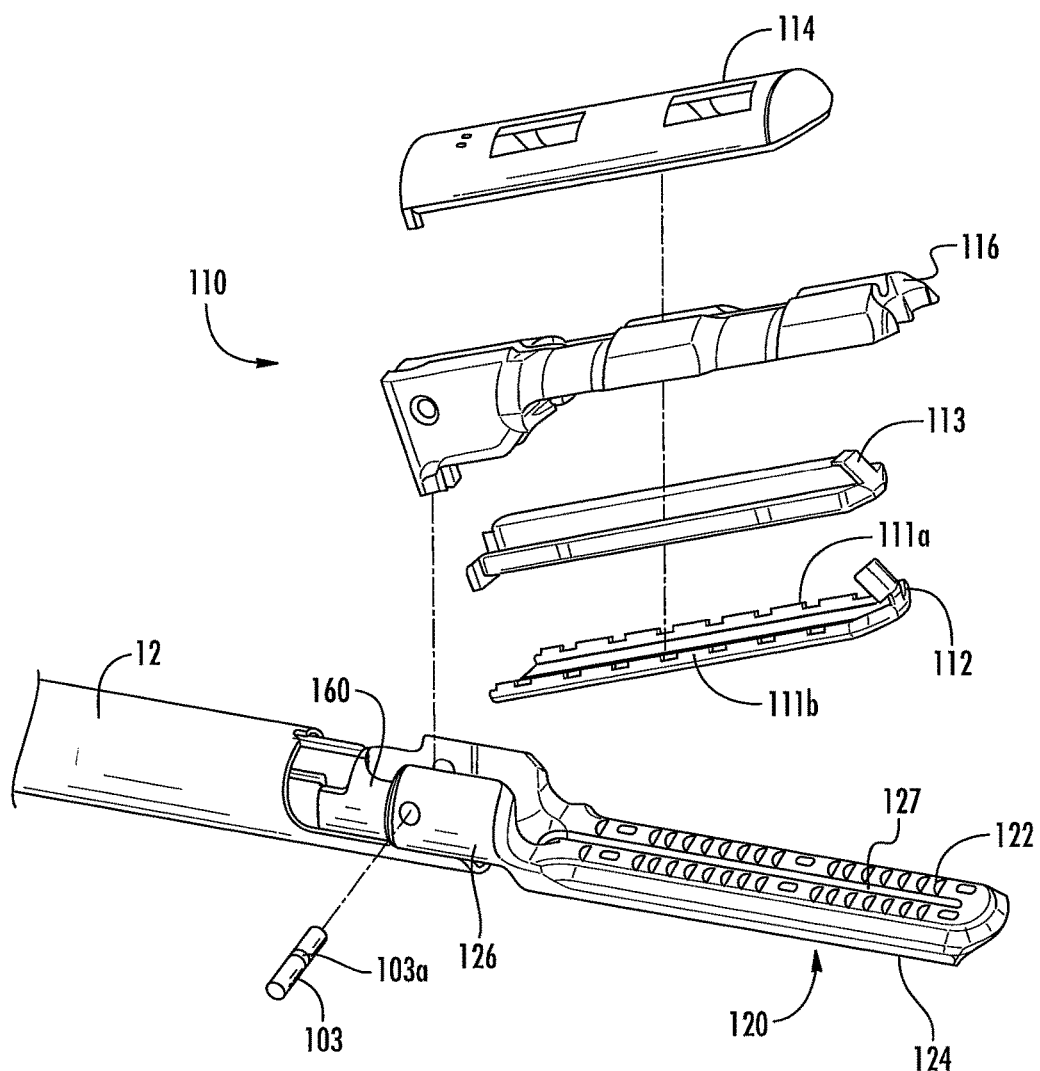
FIG. 4 is a side, perspective view of the end effector assembly of FIG. 3 with a jaw member shown with parts separated.
Figure 5:
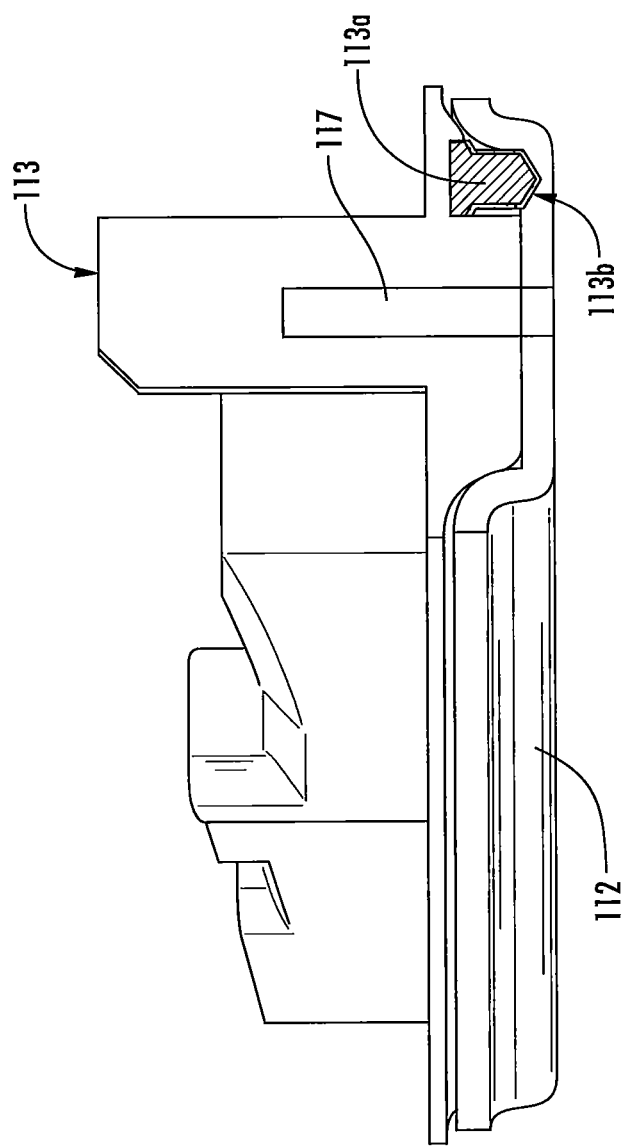
FIG. 5 is a rear perspective view of an exemplary embodiment of a jaw member in accordance with the present disclosure including a multi-shot 3D molded electrical circuit.

Referring to FIGS. 4 and 5, the jaw member 110 includes a jaw frame 116 that has an insulative cover 114, an electrically conductive plate 112, and an insulative spacer 113. The cover 114 is dimensioned to securely engage the electrically conductive plate 112. More specifically, the electrically conductive plate 112 includes a series of upwardly extending flanges 111a and 111b that are designed to matingly engage the cover 114. The cover 114 is dimensioned to engage the outer periphery of the frame 116 in a slip-fit manner The electrically conductive plate 112 of jaw member 110 is pronounced from jaw frame 116 such that tissue is grasped between opposing electrically conductive plates 112, 122 when jaw members 110 and 120 are in the closed position.

As shown in FIG. 5, the insulative spacer 113 includes rib 113a with a conductive strip 113b integrally formed on a surface thereof facing and in contact with the electrically conductive plate 112. The conductive strip 113b is configured to be in selective electrical communication with the generator (not shown) as detailed below to enable energization of the electrically conductive plate 112.

The configuration of jaw member 110 provides that the electrically conductive plate 112 is substantially surrounded by insulating cover 114. The cover 114, the electrically conductive plate 112, the insulative spacer 113, and the jaw frame 116 are configured and dimensioned to limit and/or reduce many of the known undesirable effects related to tissue sealing, e.g., flashover, thermal spread, and stray current dissipation.

Figure 7:
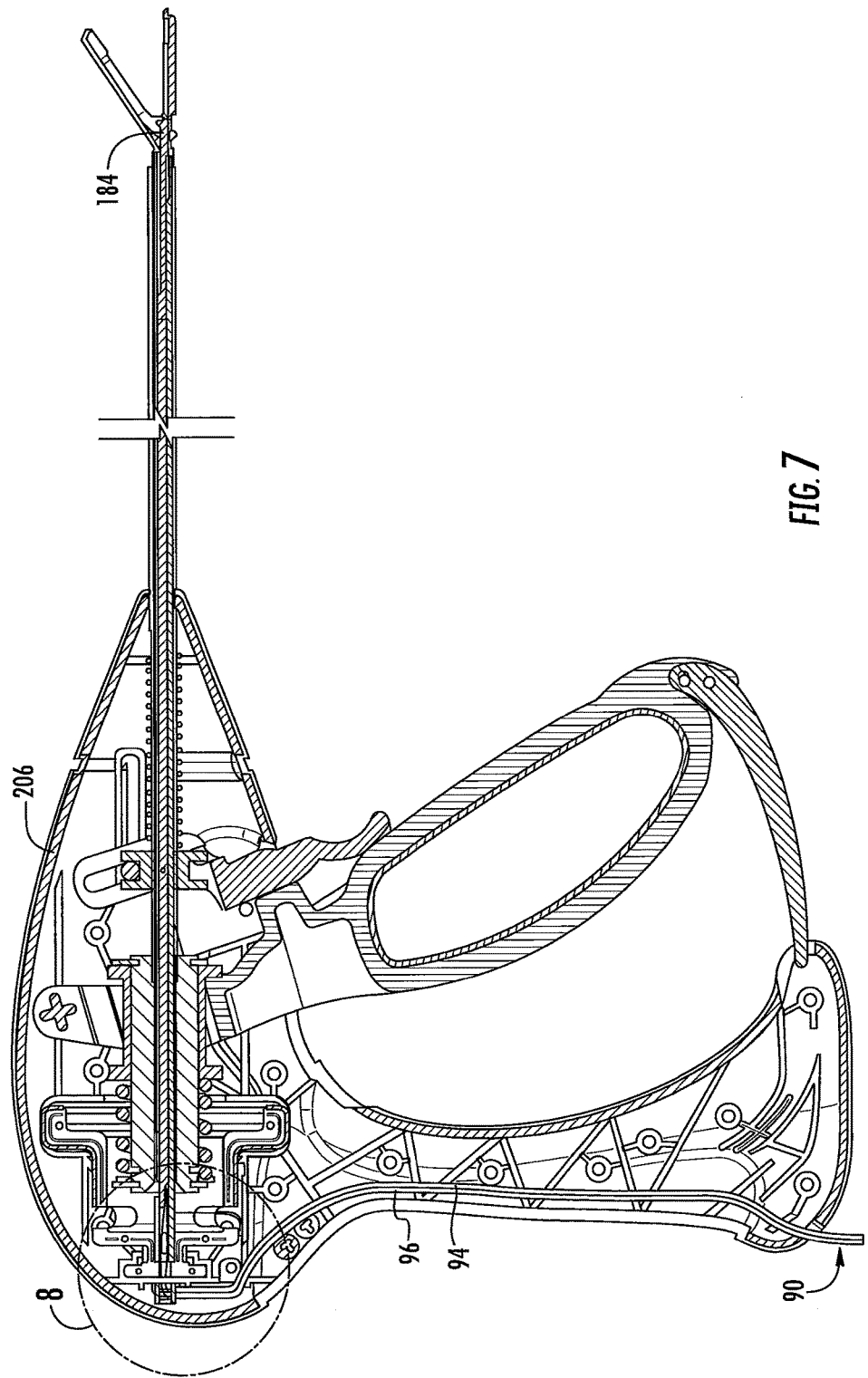
FIG. 7 is a side cross-sectional view of the surgical instrument of FIG. 1 taken along the longitudinal axis thereof.

The electrically conductive plate 112 and the insulative spacer 113, when assembled, cooperate to form a longitudinally oriented knife channel 117 defined therethrough for reciprocation of a knife blade 184 (FIG. 7). The knife channel 117 cooperates with a corresponding knife channel 127 defined in the stationary jaw member 120 to facilitate longitudinal extension of the knife blade 184 (FIG. 7) along a cutting plane to effectively and accurately separate tissue along a formed tissue seal, otherwise treated tissue, or simply in instances where only tissue cutting is desired, as detailed below.

Jaw member 120 includes similar elements to jaw member 110 such as a jaw frame 126 that has an insulative cover 124 and an electrically conductive plate 122 that is dimensioned to securely engage the cover 124. Likewise, the electrically conductive plate 122 includes a longitudinally oriented knife channel 127 defined therethrough for reciprocation of the knife blade 184 (FIG. 7). Jaw member 120 further includes an insulative spacer (not shown, similar to spacer 113) disposed between the electrically conductive plate 122 and the jaw frame 126.

Jaw member 120 is fixed to the end of a rotating tube 160 that is part of the rotating assembly 80 such that rotation of the tube 160 imparts rotation to the end effector assembly 100. More particularly, fixed jaw 120 is welded to the rotating tube 160, or may be engaged thereto in any suitable manner. Alternatively, end effector assembly 100 may be configured as a bilateral assembly e.g., wherein both jaw members 110, 120 are movable.

Figure 6:
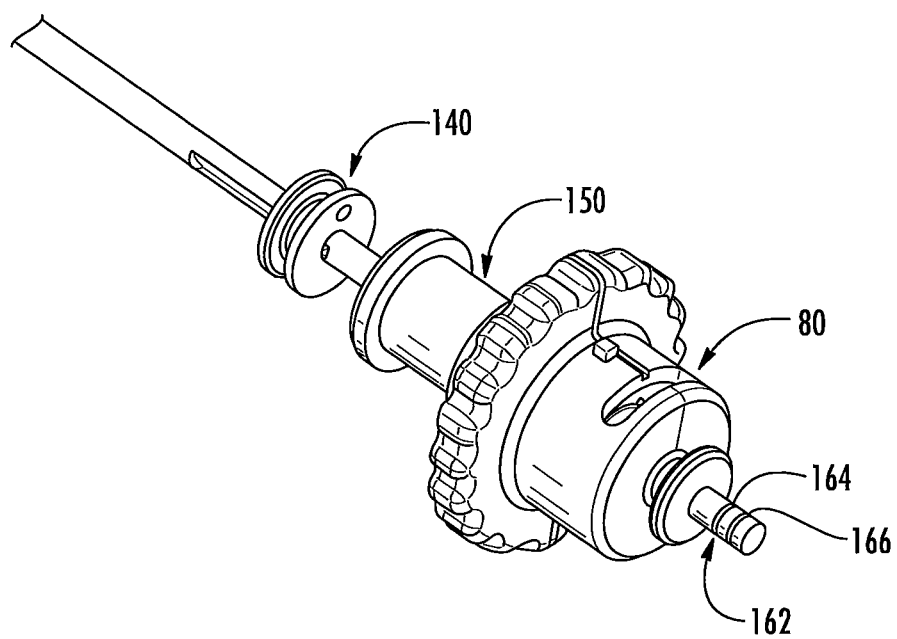
FIG. 6 is a rear perspective view of the proximal end of the inner assembly shown in FIG. 2.
Figure 8:
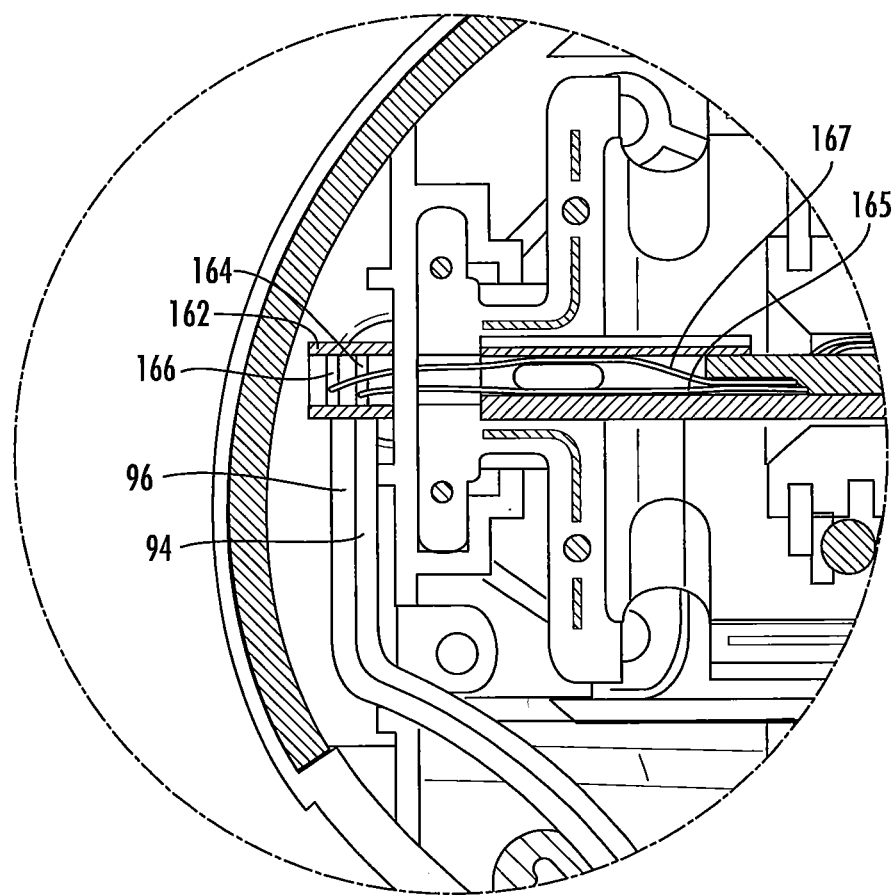
FIG. 8 is an enlarged view of the detail area "8" shown in FIG. 7.

Referring additionally to FIG. 6, a proximal portion 162 of the tube 160 includes first and second tube contacts 164, 166 that are disposed about the outer surface of the proximal portion 162. The first tube contact 164 is electrically coupled to a first cable lead 165 (FIG. 8), and the second tube contact 166 is electrically coupled to a second cable lead 167 (FIG. 8). The first and second cable leads 165, 167 are disposed within and extend through the rotating tube 160. The first cable lead 165 carries a first electrical potential through the tube 160 to the conductive strip 113b of the movable jaw 110 and, ultimately, to electrically conductive plate 112. In embodiments, the first cable lead 165 engages a conductive strip 103a disposed around the pivot pin 103 (FIG. 4) and the proximal end of the conductive strip 113b engages the conductive strip 103a to electrically couple the conductive strip 113b to the first cable lead 165. The second cable lead 167 carries a second electrical potential through the tube 160 to a second conductive strip (not shown) of the fixed jaw 120 and, ultimately, to electrically conductive plate 122.

The first and second tube contacts 164, 166 may be formed using a multi-shot 3D injection molding process as detailed below. By forming the first and second tube contacts 164, 166 on the outer surface of the proximal portion 162 of the rotating tube 160, the rotating tube 160 may be continuously rotated in either direction without damaging electrical connectors, i.e., electrical wires, connected to a source of electrosurgical energy and the first and second cable leads 165, 167.

Referring to FIGS. 7 and 8, the half 20b of the housing 20 includes electrical paths 94, 96 integrally formed on the inner surface thereof. The housing 20 and the electrical paths 94, 96 may be manufactured using a multi-shot 3D injection molding process as detailed below. The electrical paths 94, 96 are selectively in electrical communication with the first and second electrical contacts 164, 166, respectively. Each half 20a, 20b of the housing 20 includes an activation button 200 (FIG. 1) to selectively engage the first and second electrical paths 94, 96 with the first and second electrical contacts 164, 166. By including an activation button 200 on each half 20a, 20b of the housing, the surgical instrument 10 may be used as either a left-handed or a right-handed instrument. In embodiments, the electrical paths 94, 96 are disposed on the half 20a of the housing 20 in addition to or as an alterative to the half 20b of the housing 20.

The first electrical path 94 extends from a lead within the cable 90 with the first electrical potential and the second electrical path 96 extends from a lead within the cable 90 with the second electrical potential.

The button 200 permits the user to selectively activate sealing plates 112, 122 of end effector assembly 100 in a variety of different orientations, i.e., multi-oriented activation, and in both a left and right hand configurations.

The jaw members 110 and 120 are electrically isolated from each other such that electrosurgical energy is effectively transferred through tissue clamped therebetween to treat tissue, e.g., form a tissue seal. Each jaw member 110, 120 includes a conductive strip, e.g., the conductive strip 113b of jaw member 110, disposed therethrough that transmits electrosurgical energy to the electrically conductive plates 112, 122. The conductive strip 113b of the moveable jaw member 110 is electrically coupled to the conductive trace 103a about the outer surface of a pivot pin 103 and cable lead 165 is electrically coupled to the electrical trace 103a. This coupling permits electrical communication between the first cable lead 165 and the conductive strip 113b of the jaw member 110 while permitting rotation of the jaw member 110 about the pivot pin 103. This isolates the electrically conductive plate 112 from the remaining operative components of the end effector assembly 100, jaw member 120, and shaft 12. The two electrical potentials are isolated from each other by virtue of an insulative sheathing surrounding the first and second cable leads 165, 167. Utilizing the conductive trace 103a about the outer surface of pivot pin 103 and the rotating tube 160 to carry the first and second electrical potentials not only electrically isolates each jaw member 110 and 120, but also allows the jaw members 110 and 120 to pivot about pivot pin 103 without straining or possibly tangling the first and second cable leads 165, 167. The second cable lead 167 may be connected directly to the second conductive strip (not shown) of jaw member 120.

Figure 9:
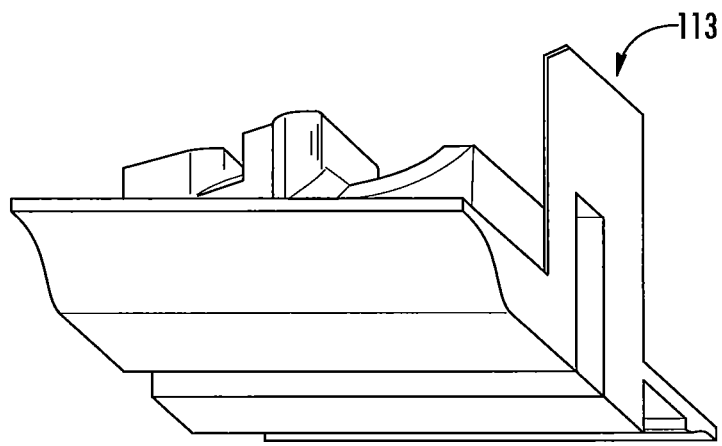
FIGS. 9-11 are rear perspective views illustrating the multi-shot 3D molding process of the present disclosure utilized to form the jaw member shown in FIG. 5.
Figure 10:
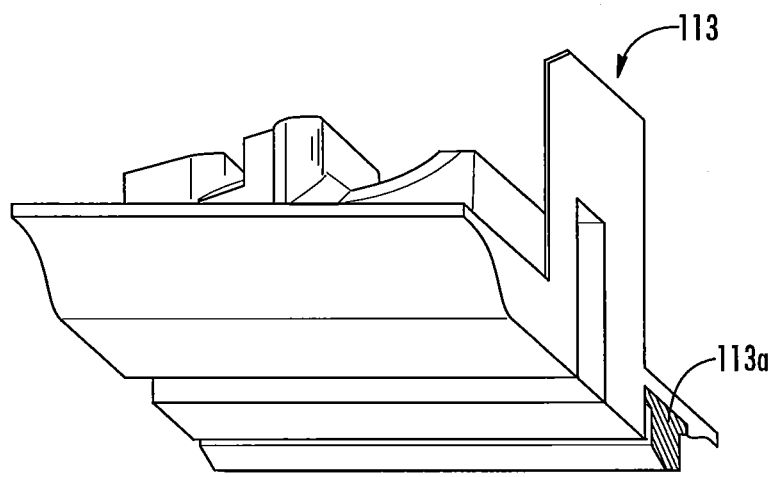
Figure 11:
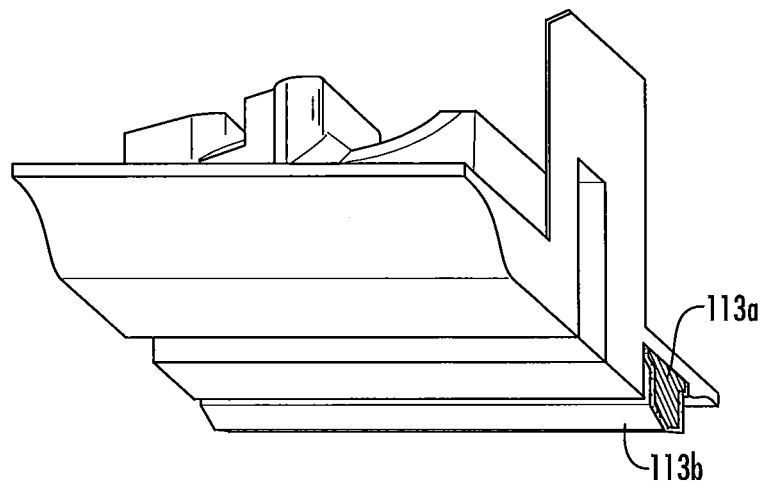

Referring to FIGS. 9-11, the multi-shot 3D injection molding process used to manufacture insulative spacer 113 with an integrally formed conductive strip 113b for the jaw member 110 in accordance with the present disclosure is described in detail. This process may also be used to manufacture the insulative spacer (not shown) with an integrally formed conductive strip (not shown) for the jaw member 120, the pivot pin 103 with an integrally formed conductive trace 103a, the rotating tube 160 with the integrally formed conductive contacts 164, 166, and the housing halves 20a, 20b with integrally formed conductive paths 94, 96. As shown in FIG. 9, a first shot of a non-conductive material, e.g., a polymer, forms the insulative spacer 113. A second shot creates rib 113a including palladium patterns or traces on the surface of the insulative material formed during the first shot as shown in FIG. 10. The spacer 113 including the rib 113a then undergoes a metallization step to create a bond between a conductive metal and the palladium patterns. The metallization step may include dipping the spacer 113 including the rib 113a into an electroless bath. During the metallization step, the conductive metal reacts with the palladium patterns 113a to form the conductive strip 113b on the surface of the rib 113a. The conductive metal may be one of copper, silver, nickel, gold, or any other suitable conductive metal. Thus, a conductive "lead" is readily and integrally formed on an insulator, e.g., insulative spacer 113.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. An end effector assembly comprising:
   a first jaw member including a first electrically conductive plate; and
   a second jaw member including a second electrically conductive plate, the first and second jaw members being operably moveable relative to one another between an open position and a clamped position wherein the first and second electrically conductive plates oppose each other, the first and second electrically conductive plates being configured to conduct energy through tissue clamped therebetween, the first jaw member further including:
      a first insulative spacer having a rib and a conductive strip, the rib extending from a surface of the first insulative spacer towards the first electrically conductive plate, the conductive strip integrally formed on a surface of the rib contacting the first electrically conductive plate, the conductive strip configured to transmit a first electrical potential to the first electrically conductive plate.

2. The end effector assembly of claim 1, wherein the second jaw member includes a second insulative spacer having a rib and a conductive strip, the rib extending from a surface of the second insulative spacer towards the second electrically conductive plate, the conductive strip integrally formed on a surface of the rib contacting the second electrically conductive plate, the conductive strip configured to transmit a second electrical potential to the second electrically conductive plate.

3. The end effector assembly of claim 1, wherein the second jaw member is fixed and the first jaw member is moveable.

4. A surgical instrument comprising:
   a housing;
   a shaft extending distally from the housing; and
   an end effector assembly positioned at the distal end of the shaft, the end effector assembly including:
      a first jaw member including a first electrically conductive plate; and
      a second jaw member including a second electrically conductive plate, the first and second jaw members being operably moveable relative to one another between an open position and a clamped position wherein the first and second electrically conductive plates oppose each other, the first and second electrically conductive plates being configured to conduct energy through tissue clamped therebetween, the first jaw member further including:
         a first insulative spacer having a rib and a conductive strip, the rib extending from a surface of the first insulative spacer towards the first plate, the conductive strip disposed on a surface of the rib contacting the first electrically conductive plate, the conductive strip configured to transmit a first electrical potential to the first electrically conductive plate.

5. The surgical instrument of claim 4, wherein the second jaw member includes a second insulative spacer having a rib and a conductive strip, the rib extending from a surface of the second insulative spacer towards the second electrically conductive plate, the conductive strip disposed on a surface of the rib contacting the second electrically conductive plate, the conductive strip configured to transmit a second electrical potential to the first electrically conductive plate.

6. The surgical instrument of claim 5 further including a first electrical path for transmitting the first electrical potential to the conductive strip of the first insulative spacer and a second electrical path for transmitting the second electrical potential to the conductive strip of the second insulative spacer, the first and second electrical paths integrally formed on an inner surface of the housing.

7. The surgical instrument of claim 6 further comprising a rotating assembly including a tube disposed within the housing and the shaft, the tube having first and second tube contacts disposed on a proximal end thereof, the first tube contact selectively electrically couplable with the first electrical path and the second tube contact selectively electrically couplable with the second electrical path.

8. The surgical instrument of claim 7 further comprising first and second electrical leads, the first electrical lead in electrical communication with the first tube contact and electrically coupled to the conductive strip of the first insulative spacer for transmitting the first electrical potential from the first electrical path to the first electrically conductive plate, the second electrical lead in electrical communication with the second tube contact and electrically coupled to the conductive strip of the second insulative spacer for transmitting the second electrical potential from the second electrical path to the second electrically conductive plate.

9. The surgical instrument of claim 8, wherein the first and second electrical leads are disposed within the tube of the rotating assembly.

10. The surgical instrument of claim 7 further comprising an electrosurgical cable for transmitting energy from a generator to the instrument, wherein the first electrical path is disposed between the electrosurgical cable and the first tube contact, and wherein the second electrical path is disposed between the electrosurgical cable and the second tube contact.

* * * * *